United States Patent [19]

Podder et al.

[11] Patent Number: 4,665,233

[45] Date of Patent: May 12, 1987

[54] PROCESS FOR THE PREPARATION OF 4-NITRODIPHENYLAMINES

[75] Inventors: Chiraranjan Podder, Dormagen; Harro Schlesmann, Odenthal, both of Fed. Rep. of Germany

[73] Assignee: Bayer Aktiengesellschaft, Leverkusen, Fed. Rep. of Germany

[21] Appl. No.: 798,906

[22] Filed: Nov. 18, 1985

[30] Foreign Application Priority Data

Nov. 30, 1984 [DE] Fed. Rep. of Germany ....... 3443679

[51] Int. Cl.$^4$ ............................................. C07C 85/04
[52] U.S. Cl. .................................................... 564/406
[58] Field of Search ......................................... 564/406

[56] References Cited

U.S. PATENT DOCUMENTS

| 3,055,940 | 9/1962 | Merz | 564/406 |
| 3,121,736 | 2/1964 | Luvisi et al. | 564/406 |
| 3,277,175 | 10/1966 | Clemens | 564/406 |
| 4,122,118 | 10/1978 | George et al. | 564/406 |
| 4,155,936 | 5/1979 | Sturm | 564/406 |
| 4,404,400 | 9/1983 | Heise et al. | 564/406 |

Primary Examiner—Paul F. Shaver
Attorney, Agent, or Firm—Connolly and Hutz

[57] ABSTRACT

An improved process for the preparation of 4-nitrodiphenylamines by the reaction of 4-nitrohalobenzenes with primary aromatic amines in the presence of potassium carbonate and copper compounds is characterized in that sulpholane dimethylsulphone, dimethylacetamide, diethylacetamide, tetramethylurea, tetraethylurea or mixtures thereof are used as solvents and 3 to 5 mol of amine are used per mol of halogenated nitrobenzene, from 1.2 to 2 mol of said amine being added before the beginning of the reaction and the remainder during the reaction at such a rate that the molar excess of unreacted amine over unreacted halogenated nitrobenzene is constantly at least 100%.

6 Claims, No Drawings

PROCESS FOR THE PREPARATION OF 4-NITRODIPHENYLAMINES

This invention relates to a process for the preparation of 4-nitrodiphenylamines by the reaction of 4-nitrohalobenzenes with primary aromatic amines in the presence of potassium carbonate and copper compounds.

The reaction of halonitrobenzenes with aromatic amines has been known for a long time. According to DE-PS No. 185 663, the reaction is carried out in the presence of alkali metal carbonates and copper compounds as catalysts.

It is also known that the extremely slow reaction can be accelerated by using potassium carbonate and removing the water of reaction by azeotropic distillation. According to Example 1 of U.S. Pat. No. 2,927,943, moderately pure 4-nitrodiphenylamine was obtained in a yield of 73% of the theoretical under these conditions over a reaction time of 21 hours. It is also known from U.S. Pat. No. 4,155,936 that the reaction of halonitrobenzenes with primary aromatic amines not only has the disadvantage of long reaction times but the further disadvantages of contamination of the nitrodiphenylamine due to the formation of considerable quantities of tars and byproducts and the formation of nitrobenzene due to reductive dehalogenation (see U.S. Pat. No. 3,313,854, column 3, lines 64, 65).

To overcome these disadvantages, it has already been proposed to add cocatalysts, solubilizing agents and dipolar aprotic solvents to the reaction mixture.

Formanilide according to U.S. Pat. No. 3,313,854, acetanilide according to DE-AS No. 1 518 307, salicylic anilide according to DE-AS No. 1 117 594 and ε-caprolactam according to JP No. 8 122 751, however, have only a slight effect.

The proposals made in U.S. Pat. No. 3,121,736 (addition of aminocarboxylic acids, of alkyldiaminopolycarboxylic acids and salts, of disalicylaldiaminoalkanes, of o-hydroxybenz aminophenols of polyphosphates, carboxymethylmercaptosuccinic acid or Schiff's bases of salicylaldehydes), in JP-PA No. 8 240 445 (addition of benzyl trimethylammonium bromide, benzyltributylphosphonium chloride, benzyltriphenylphosphonium chloride, tetramethylammonium chloride, tetrabutylphosphonium chloride), or in DE-OS No. 3 137 041 (addition of imidazole or imidazoline, pyrimidine, bicyclic amidine, triazine, phenanthroline, dipyridine, bisquinoline) give rise to problems in working up the product.

The use of caesium compounds according to DE-OS No. 3 246 151 provides improved yields but considerably increases the cost of the process.

The addition of polyethers of various structures described in U.S. Pat. No. 4,155,936, JP-PA No. 80 100 342 and 82 02 243 also fails to provide any improvement.

Other additives which, however provide no improvement, have been described in U.S. Pat. No. 3,055,940 (dimethylformamide and hexamethylphosphoric acid triamide), U.S. Pat. No. 3,277,175, (dimethylsulphoxide), DE-OS No. 2 633 811 (N-methylpyrrolidone) and JP-PA No. 71/09452 (diethylformamide).

A process has now been found for the preparation of 4-nitrodiphenylamines corresponding to formula (I)

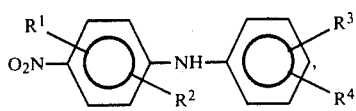

wherein $R^1$, $R^2$, $R^3$ and $R^4$ are identical or different and stand for hydrogen or an alkyl group with 1 to 9 carbon atoms by the reaction of halonitrobenzenes corresponding to formula (II)

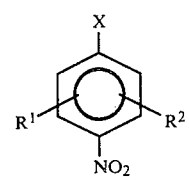

wherein X stands for chlorine or bromine and in which $R^1$ and $R^2$ have the meanings indicated above with primary aromatic amines corresponding to formula (III)

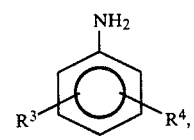

wherein $R^3$ and $R^4$ have the meaning indicated above in the presence of potassium carbonate and copper compounds, in which process sulpholane, dimethylsulphone, dimethylacetamide, diethylacetamide, tetramethylurea, tetraethylurea or mixtures thereof are used as solvents and 3 to 5 mol of amine are used per mol of halonitrobenzene, from 1.2 to 2 mol of which amine are added before the beginning of the reaction and the remainder is added during the reaction at such a rate that the molar excess of unreacted amine over unreacted halonitrobenzene is constantly at least 100%.

The alkyl groups of formula (I) are preferably those with 1 to 3 carbon atoms.

The process is preferably used for the preparation of 4-nitrodiphenylamine from 4-nitrochlorobenzene and aniline.

The following are examples of copper catalysts which may be used in the process according to the invention: Copper-(I)-iodide, copper-(I)-chloride, copper-(II)-chloride, copper-(I)-bromide, copper-(II)-bromide, copper-(I)-cyanide, copper-(I)-oxide, copper-(II)-oxide, copper-(II)-carbonate, basic copper-(II)-carbonate, copper-(II)-sulphate, copper-(II)-nitrate, copper-(II)-formate, copper-(II)-acetate and organic and inorganic coordination compounds of monovalent or divalent copper. It is preferred to use copper compounds containing oxygen, such as copper-(II)-oxide, copper-(II)-carbonate, basic copper-(II)-carbonate or copper-(I)-oxide, the copper catalysts being used in a quantity of from 0.001 to 0.1 mol, preferably from 0.01 to 0.05 mol per mol of halonitrobenzene put into the process. The copper catalysts may be used singly or in mixture with one another.

Examples of suitable halonitrobenzenes include 4-nitrochlorobenzene, 4-nitrobromobenzene, 4-nitro-2-methylchlorobenzene and 4-nitro-3-methyl-chlorobenzene.

Examples of suitable primary aromatic amines include aniline, o-toluidine, m-toluidine, p-toluidine, 4-ethylaniline, 4-butylaniline, 4-isopropylaniline, 3,5-dimethylaniline and 2,4-dimethylaniline.

The aromatic amines may, of course, also be used as mixtures, in particular isomeric mixtures.

The solvents, sulpholane, dimethylsulphone, dimethylacetamide, diethylacetamide, tetramethylurea and tetraethylurea and mixtures thereof, are generally used in quantities of from 0.1 to 2 mol, preferably from 0.25 to 1.5 mol, in particular from 0.5 to 1 mol per mol of halonitrobenzene.

Rubidium and caesium compounds may be added to the reaction mixture.

Potassium carbonate may be used in the equivalent quantity or in excess, up to 1.5 times the equivalent quantity.

The water of reaction is advantageously removed from the reaction mixture by distillation with the aid of an entrainer. The entrainer used may be, for example xylene, toluene, benzene, chlorobenzene or chlorotoluene.

The process according to the invention may be carried out in the presence of additional diluents, e.g. inert hydrocarbons such as xylene, if necessary for the purpose of adjusting or maintaining the reaction temperature range. The aromatic primary amines may themselves be used for this purpose.

The reaction temperatures of the process according to the invention may vary within wide limits and are generally from 140° to 225° C., preferably 180° to 210° C.

The process according to the invention may be carried out continuously or batchwise by conventional methods.

Working up of the reaction mixture may also be carried out by various methods. The salts present in the reaction mixture may be separated by physical means at elevated temperature, such as by centrifuging or filtration. After washing with warm xylene and drying, a light grey, pulverulent solid is left behind.

Xylene, unreacted halonitrobenzene, primary aromatic amine and solvents may be completely removed from the filtrate in a rotary evaporator or in an coil evaporator under a vacuum of 5 to 50 mbar and at a temperature of 150° to 220° C., the nitrodiphenylamines being obtained in the form of melts which solidify on cooling. The mixture obtained as distillate may be used for the next reaction batch without further treatment. According to another possible method, the filtrate is partly distilled under vacuum and the nitrodiphenylamines are to a large extent separated by crystallisation. The nitrodiphenylamines are then obtained in a highly pure form directly suitable for further use. The distillate from the vacuum distillation and the mother liquor from crystallisation may be used again.

The copper catalyst may be used repeatedly. To maintain its full activity, fresh catalyst may be added in a smaller quantity than that originally used.

4-Nitrodiphenylamines may be obtained in yields of 88 to 92% and high degrees of purity with short reaction times by the process according to the invention. The formation of by-products occurs only to a slight extent in the process according to the invention.

The 4-nitrodiphenylamines prepared by the process according to the invention may readily be reduced to aminodiphenylamines by known processes and as such are valuable intermediate products, for example for the preparation of dyes or stabilizers for rubber (see U.S. Pat. No. 3,163,616).

EXAMPLE 1

157.6 g of p-nitrochlorobenzene, 186 g of aniline, 100 g of potassium carbonate, 20 ml of xylene, 2 g of copper oxide and 120 g of sulpholane were introduced into a 1-liter flask equipped with stirrer and distillation attachment with water separator.

The reaction mixture was heated to 195° C. with stirring. A further 186 g of aniline were then added portionwise and the contents of the flask were maintained at 195° C. until about 11 ml of water had separated, and the 4-chloronitrobenzene content was determined on a sample by liquid chromotography. If the 4-chloronitrobenzene content was found to be less than 1.5% of the original quantity, the reaction was stopped by cooling; otherwise, the reaction was continued until this value was obtained. The total reaction time was 6.7 to 7 hours.

The reaction mixture was filtered while hot and the solid was washed with xylene. The xylene phase was combined with the filtrate. The volatile constituents were distilled off the organic solution at 10 to 15 mbar at 190° to 200° C. 220 g of 4-nitrodiphenylamine were obtained as residue. According to liquid chromatographic analysis, this contained 87% by weight of pure product, corresponding to a yield of 89%, based on 4-nitrochlorobenzene.

EXAMPLE 2

In the reaction mixture described in Example 1, 47 g of dimethylsulphone were used instead of sulpholane.

The reaction was carried out in exactly the same manner as in Example 1. The total reaction time was 8 to 8.5 hours.

The reaction mixture was worked up as in Example 1. 218 g of 4-nitrodiphenylamine were obtained. According to liquid chromatographic analysis, this had a product content of 88% by weight, corresponding to an 89% yield, based on 4-nitrochlorobenzene.

EXAMPLE 3

44 g of Dimethylacetamide were added instead of sulpholane to the reaction mixture described in Example 1.

The reaction was carried out in exactly the same manner as in Example 1. The total reaction time was 6.5 hours.

The reaction mixture was worked up in the same manner as in Example 1. Distillation was carried out at 10 to 15 mbar at 150° to 160° C. 216 g of 4-nitrodiphenylamine were obtained. According to liquid chromatographic analysis, this contained 91% by weight, corresponding to a 92% yield based on 4-nitrochlorobenzene.

EXAMPLE 4

58 g of Tetramethylurea were used instead of sulpholane in the reaction mixture described in Example 1.

The reaction was carried out in exactly the same manner as in Example 1. The total reaction time was 7 to 7.5 hours. The reaction mixture was worked up as described in Example 3. 214 g of 4-nitrodiphenylamine were obtained. According to liquid chromatographic analysis, this contained 88% by weight of product, corresponding to an 88% yield based on 4-nitrochlorobenzene.

We claim:

1. A process for the preparation of 4-nitrodiphenylamines by the reaction of 4-nitrohalobenzenes with primary aromatic amines in the presence of potassium carbonate and copper compounds, in which process sulpholan, dimethylsulphone, dimethylacetamide, diethylacetamide, tetramethylurea, tetraethylurea or mixtures thereof are used as solvent and 3 to 5 mol of amine are used per mol of halonitrobenzene, 1.2 to 2 mol of which amine are added before the beginning of the reaction and the remainder during the reaction at such a rate that the molar excess of unreacted amine over unreacted halonitrobenzene constantly amounts to at least 100%.

2. A process according to claim 1, characterised in that the 4-nitrodiphenylamines correspond to the following formula

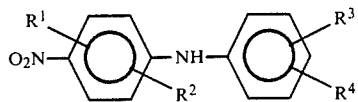

wherein $R^1$, $R^2$, $R^3$ and $R^4$ may be identical or different and stand for hydrogen or an alkyl group with 1 to 9 carbon atoms.

3. A process according to claim 1, characterised in that 4-nitrochlorobenzene is reacted with aniline to form 4-nitrodiphenylamine.

4. A process according to claim 1, characterised in that the solvents are used in a quantity of from 0.1 to 2 mol and the copper catalyst in a quantity of from 0.001 to 0.1 mol, based in each case on 1 mol of halonitrobenzene.

5. A process according to claim 1, characterised in that the reaction is carried out at 140° to 225° C.

6. A process according to claim 1, characterised in that the water of the reaction is removed by distillation with the aid of an entrainer.

* * * * *